United States Patent [19]

Characklis et al.

[11] 4,396,300
[45] Aug. 2, 1983

[54] METHOD AND APPARATUS FOR DETERMINING THE HEAT TRANSFER CHARACTERISTICS OF A TUBE

[75] Inventors: William G. Characklis; Frank L. Roe; Nicholas Zelver, all of Bozeman, Mont.

[73] Assignee: Bridger Scientific, Inc., Bozeman, Mont.

[21] Appl. No.: 259,466

[22] Filed: May 1, 1981

[51] Int. Cl.³ ............................................. G01N 25/00
[52] U.S. Cl. ......................................................... 374/43
[58] Field of Search ................... 73/15 R, 15 A, 112, 73/12; 374/7, 43

[56] References Cited

U.S. PATENT DOCUMENTS

| | | | |
|---|---|---|---|
| 3,229,499 | 1/1966 | Shayeson et al. | 73/15 |
| 3,913,379 | 10/1975 | Hausler | 73/15 |
| 3,918,300 | 11/1975 | Weisstuch et al. | 73/15 |

Primary Examiner—Herbert Goldstein
Attorney, Agent, or Firm—Eric P. Schellin

[57] ABSTRACT

A test apparatus is provided for testing the heat transfer resistance of a tube, such as a tube of a heat exchanger, the apparatus including a heating means, such as a block of metal surrounding and engaging a part of the tube, with an electric heater for heating the block, the block including at least two termistors at different distances from the tube to measure heat flux. A pump causes water to flow through the tube, and a thermistor measures the water temperature. A flow meter and a pressure drop sensor for sensing the drop in pressure across the block are also provided. The measuring devices other than the flow meter provide, preferably, analog output signals, which are converted and supplied to a computer for computation of total heat transfer resistance, convective heat transfer resistance, conductive heat transfer resistance of the tube and friction factor.

14 Claims, 4 Drawing Figures

OUTPUT TO
ANALOG MULTIPLEXER 110

METHOD AND APPARATUS FOR DETERMINING THE HEAT TRANSFER CHARACTERISTICS OF A TUBE

TECHNICAL FIELD

The present invention is related to a measuring and testing apparatus, and more particularly to a measuring and testing apparatus which will measure the heat transfer and frictional resistance characteristics of a tube such as used in a water-tube heat exchanger.

BACKGROUND ART

Apparatus has been provided to determine heat conductance of tubes. A review of the prior art apparatus and methods is provided in an article in "Condenser Biofouling," 1980, by J. G. Knudsen, Prof. of Chemical Eng., Oregon State University, Corvallis, Ore.

DISCLOSURE OF INVENTION

The present invention is directed to an apparatus for measuring the heat transfer characteristics of a tube through which a liquid such as water is passed. There is associated with the tube a heater which includes a block of heat conducting material, as aluminum, which is clamped to the exterior of the tube being tested along a portion of its length, which is the test section. This block has associated with it an electric heater. To measure the heat flux, there are embedded in the block, at different radii from its internal face, a pair of temperature probes, such as a pair of thermistors. Water is forced through the tube, passing through an entrance section in advance of the test section, from a pump which has its discharge connected to one end of the tube and its inlet connected to the other end of the tube, there being a bypass circuit with a motorized control valve in it around the pump, so as to by-pass a variable amount of water from the pump. The tube is insulated, and a small electric heater is placed on the tube, beneath the insulation, between the end of it and the heating block. Ports are provided in the tube on either side of the heating block, and a pressure drop sensor is connected to the ports. A flow meter is provided to measure the rate of water flowing through the tube.

Preferrably, the measuring devices provide output signals, which are converted, where necessary, to digital signals, which are fed to a computer. The computer calculates the total heat transfer resistance, the convective heat transfer resistance and the conductive heat transfer resistance, thereby providing an indication of the reduction in thermal efficiency of the tube due to build-up of contaminants on the interior wall of the tube, this being accomplished together with a calculation of the friction factor of the tube.

BEST MODE FOR CARRYING OUT THE INVENTION

Figure 1:
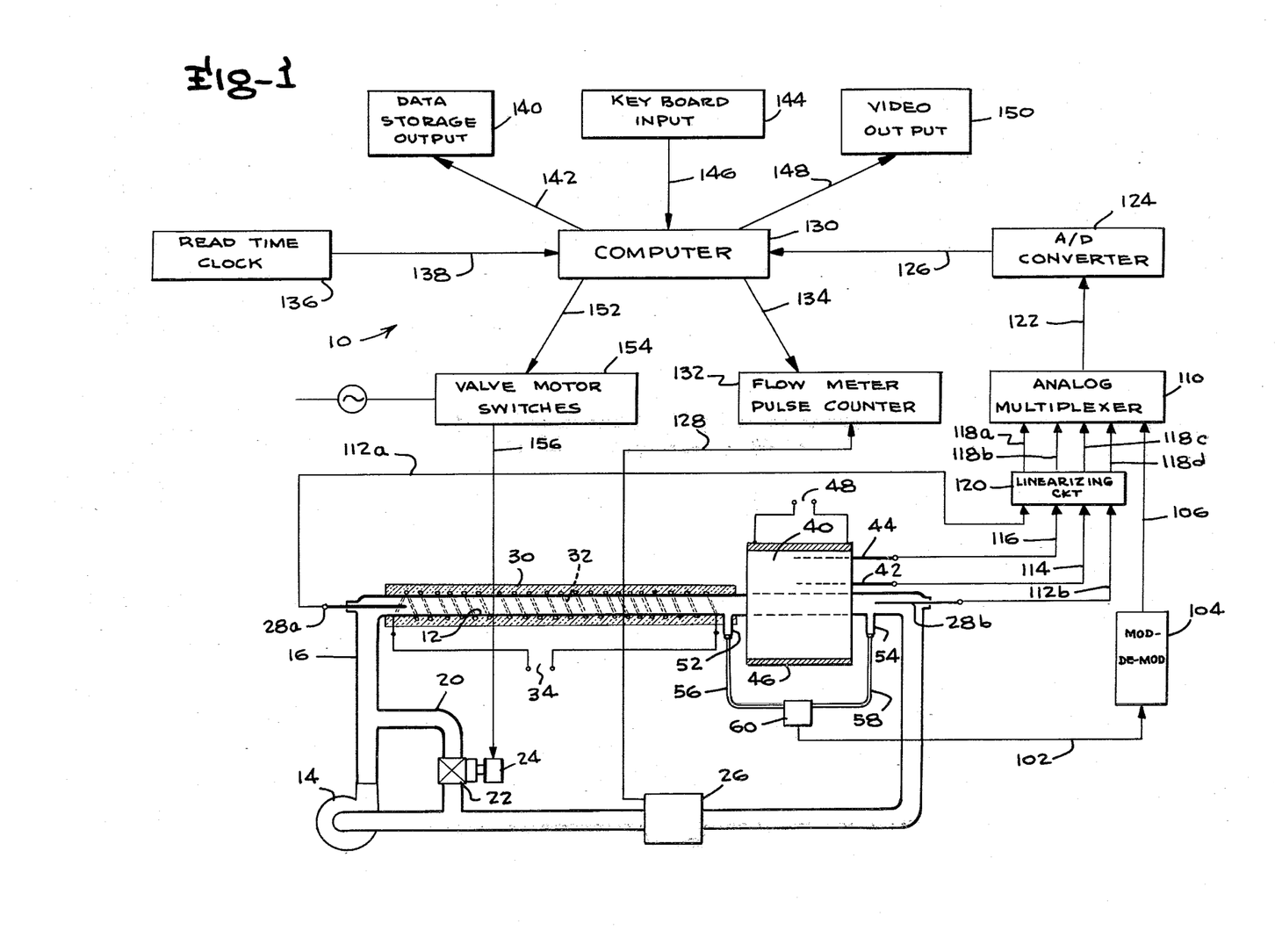
FIG. 1 is a schematic view, partly diagrammatic, of an apparatus in accordance with the present invention.

Referring now to the drawings, wherein like or corresponding parts are designated by like or corresponding reference numerals throughout the several views, there is shown in FIG. 1 an apparatus 10 in accordance with the present invention, the apparatus 10 including a tube 12 which is of heat conducting material, and of conventional construction as used in tubular heat exchangers. The tube 12 may, for example, be a sample tube of the same alloy as in a particular tubular heat exchanger, for use as a specimen for various test purposes, or may be a new alloy, being tested.

A pump 14 is provided, having its outlet connected by a conduit 16 to the inlet end of the entrance section of the tube 12, the outlet end of the tube 12 being connected by a conduit 18 to the inlet of the pump. A by-pass conduit 20 bypasses the pump 14, and has therein a valve 22 controlled by a motor 24. Alternatively the valve can be in series with the pump and test section. In the conduit 18 there is a flow meter 26 of known construction which produces pulses in proportion to the velocity, and therefore the rate, of water flow through the closed circuit, including particularly the tube 12.

The pump 14 may be a separate pump forming a part of the test equipment, or may be the pump of a power plant or the like; in that case, the tube 12 is mounted in the power plant, in series with the tube of the heat exchanger, and thereby receives water from the same pump which forces water through the tubes of the heat exchanger.

The tube 12 is provided with one or more thermometers 28a, 28b, herein illustrated as being of the electrical type and called thermistors. Thus, the output of the thermometers 28a, 28b is in the form of an electrical analog signal.

The tube 12 is covered over the entry section, in advance of the test section, with insulating material 30, beneath which is an electrical heater 32 which is connected to a suitable source of electricity by the contacts 34. The heater 32 serves to create a fully developed thermal gradient in the water flowing through the pipe 12 to the test section as described below.

In order to make it possible to measure the thermal resistance to the introduction of a large quantity of heat into the water in the tube 12 in a short period of time, there is provided a high thermal conductivity radial heat flow concentrator; i.e. a heating block 40 which is of a suitable heat conducting material, such as aluminum. The block 40 is preferrably annular, having an inner cylindrical face which is in engagement with the exterior surface of the test section of tube 12. The block 40 is preferrably made in two or more parts, so that it may be releasibly clamped onto the tube 12. To measure heat flux into the tube 12, embedded in the heating block 40 are a pair of thermistors 42 and 44, which are located at different radii from the axis of the heating block 40, and are therefore at different distances from an electric heater 46 which is placed in surrounding relationship to block 40 and is connected to a suitable source of electric energy through the contacts 48.

To determine the pressure drop of the water flowing in the test section of tube 12 there are provided ports 52 and 54 on either side of the block 40 and adjacent thereto, conduits 56 and 58 connecting the ports to a differential pressure transducer 60 of known construction, having an analog output proportional to the noted pressure drop.

Where the word "water" has been used herein, it will be understood that this is the liquid that is most commonly dealt with, it being recognized that other liquids also may be caused to flow in heat exchanger tubes, and cause contamination or fouling of them. The most commonly used medium is water, however, and water is known to have various impurities in it, both of mineral materials, and biological materials. Mineral materials may include various salts, carbonates, sulfates, sulfites, etc., as is well known. Either type material may be found in the water of a particular installation, or it may be possible that both types of fouling materials may be found in a particular installation. A layer of fouling material which has as its source biological materials is known as biofilm, and a layer or coating which is of mineral or innert matter is known as scale.

Both biological fouling and scaling result in reduced heat exchanger efficiency, and it is known that the resistance of a tube to conductive heat transfer is different, to a marked degree, when biofilm is present, compared to scaling.

By utilizing the value of the pressure drop and the flow rate, it is possible to determine the friction factor by the following well known formula:

$$f = 2 \frac{d\Delta p}{L\rho \bar{v}^2}$$

where
f is the friction factor,
d is the inside diameter of the tube 12,
p is the differential pressure between ports 52 and 54,
L is the length of the tube 12 across where the pressure drop is measured,
$\rho$ is the density of the fluid directed through the tube 12, and
$\bar{v}$ is the average fluid flow velocity through tube 12.

The value of Reynold's number, $N_{Re}$, is determined by the following known formula:

$$N_{Re} = \frac{\bar{v}dp}{\mu}$$

where
$N_{Re}$ is the Reynold's number,
$\mu$ is the dynamic viscosity of the fluid
d is the inner diameter of the tube through which the fluid flows,
$\rho$ is the density of the fluid, and
v is the average fluid velocity through the tube.

Utilizing the values of temperature from the thermistors 42 and 44, and the value of the bulk water temperature from 28a and 28b, the total heat transfer resistance can be calculated using the following known formula:

$$\frac{1}{U_{tot}} = \frac{2\pi r_i l(T_i - T_b)}{q}, \text{ where } q = \frac{2\pi k l(T_{ii} - T_i)}{\ln(r_{ii}/r_i)},$$

$r_i$ is the radius at 42 and $r_{ii}$ is the radious at 44,
$T_b$ is the bulk water temperature,
$T_i$ is the temperature at 42 and $T_{ii}$ is the temperature at 44,
k is the thermal conductivity of the block 40,
q is the heat flux radially inward in the block,
l is the length of the block, and
ln is the natural logarithm function Where the liquid is not water, the temperature viscosity relationship is determined from standard reference sources.

The convective heat transfer resistance, is calculated from the values of the friction factor f using the following known formula:

$$\frac{1}{U_{conv}} = \frac{0.125 f C_p^{\frac{1}{3}} R^{\frac{2}{3}} \rho \bar{v}}{\mu^{\frac{2}{3}}}$$

where
$U_{cv}$ is the convective heat transfer resistance,
f is the friction factor,
$C_p$ is the specific heat of the fluid directed through the tube 12,
R is the thermal conductivity of the fluid directed through the tube 12,
$\rho$ is the density of the fluid,
$\bar{v}$ is the average fluid flow velocity, and
$\mu$ is the dynamic viscosity of the fluid directed through the tube 12.

Since the total heat transfer resistance is the sum of the conductive heat transfer resistance and the convective heat transfer resistance, by subtracting the value of the convective heat transfer resistance from the total heat transfer resistance, the conductive heat transfer resistance is obtained.

Preferably, the values of pressure drop, water flow rate, heat flux input to tube 12 and the water temperature, are realized as electrical signals, proportional to the physical characteristic being determined. In the case of the flow meter, the output will be in pulses, and in the case of the other measurements, the output is an electrical signal which is an analogue of the value measured, and in that case, the electrical output analog signals are converted to digital signals, and then all signals are fed to a suitable computer, the output of which may be by a video readout, printout, etc., and the computer may be used to perform functions, such as regulating the by-pass valve.

Referring again to FIG. 1, the differential pressure transducer 60 is connected by conductor 102 to a modulator-demodulator 104, which is connected by a conductor 106 to an analog multiplexer 110. Thermistor 28a is connected by conductor 112a to a thermistor amplifier 120, and thermistor 28b is connected by conductor 112b to the amplifier 120. Conductors 114 and 116 connect the thermistors 42 and 44, respectively, to the transistor amplifier 120, and the latter is connected by conductors 118a, 118b, 118c and 118d to the analogue multiplexer 110. The output from analog multiplexer 110 is connected by conductor 122 to an analog-digital converter 124, the output of which is connected to the computer 130 by a conductor 126.

The flow meter 26 has a pulse output, as is well known, and this output is provided by a conductor 128 to a pulse counter 132, the output of which is connected to the computer by conductor 134. Alternatively a magnetic flow sensor can be used which has an analog signal output. A real time clock 136 is connected to computer 130 by conductor 138. A data storage output 140 is connected to computer 130 by conductor 142 and there may be provided a keyboard input 144 connected to computer 130 by a conductor 146 and a video output 150 connected to the computer 130 by a conductor 148.

The output of the computer may, through conductor 152, be directed to control switching 154 which is connected by conductor 156 to the motor 24 of bypass valve 22.

Computer 130 may be an Apple II, and may be programmed in accordance with the below described program, although it will be understood that any equivalent computer may be used.

Figure 2:
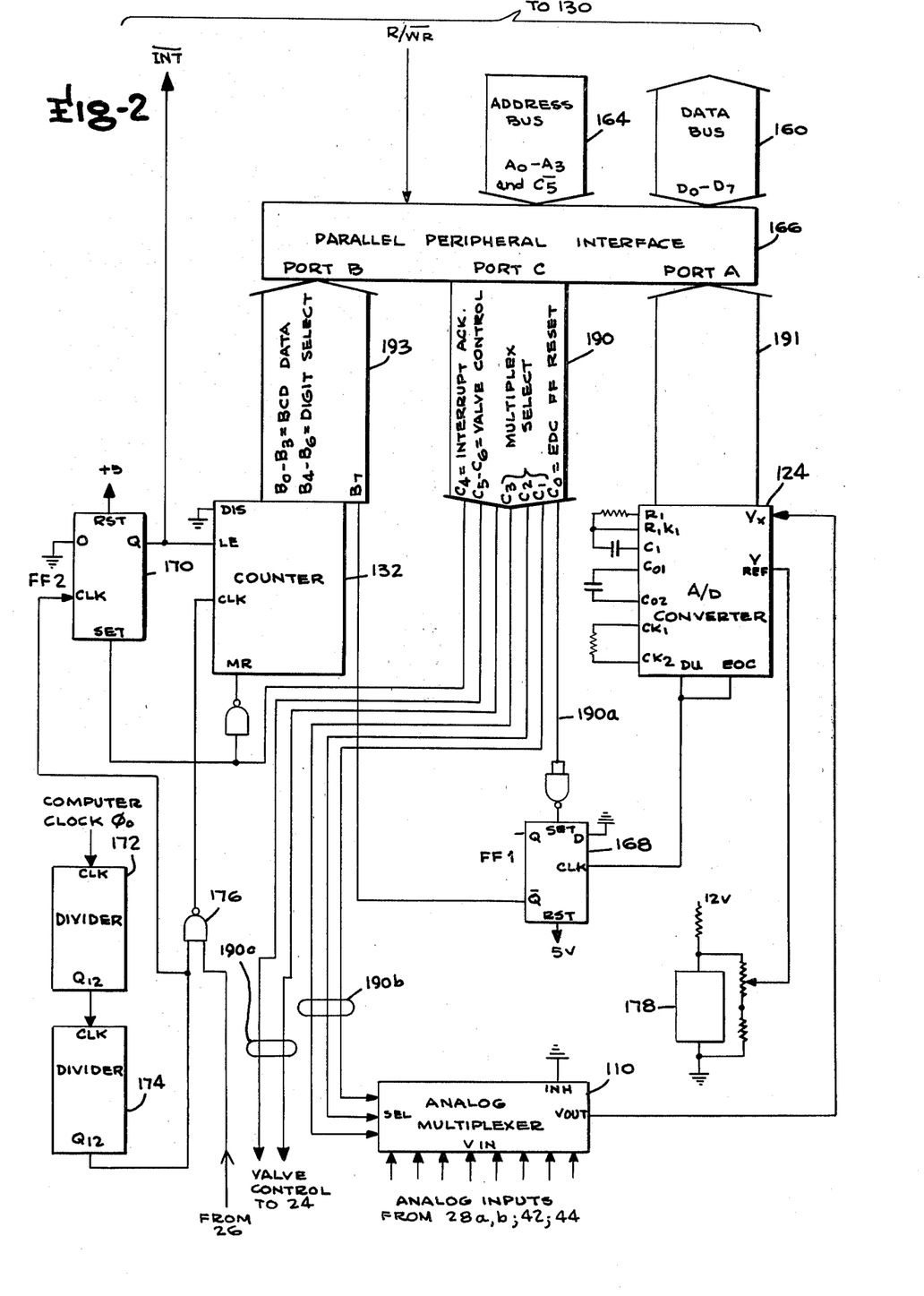
FIG. 2 is a schematic diagram of the interface circuitry which couples the measuring apparatus to the computer.

Referring now to FIG. 2, there is shown an interface circuit whereby the various sensors including the thermistors 42 and 44, the differential pressure transducer 60, the thermometers 28a and 28b, the counted pulses derived from the flow meter 26 are input to the computer 130. Generally, the computer 130 is interconnected to a parallel peripheral interface 166 whereby inputs and outputs are made to and from the computer 130. The A0-A9 and C output terminals of the computer 130 are coupled by an address bus 164 to the parallel pheripheral interface 166, whereby corresponding address signals are applied by bus 190 to the analog multiplexer 110, whereby one of the inputs as obtained from one of the formentioned thermistors 42 and 44 and thermometers 28a and 28b is applied selectively to the computer 130. In particular, the bus 190 includes a timing or setting signal applied by line 190a through an inverter to a set input of a flip flop 168. Further, digital signals are applied via lines 190b to instruct the analog multiplexer 110 to select the output of but a single temperature sensor in accordance with the signal input applied thereto. Further, the address lines 190c apply a digital signal to instruct the bypass valve 22 whether to open or to close, thereby increasing or decreasing the flow through the tube 12. As illustrated in FIG. 2, the selected or multiplexed analog output is applied to the A/D converter 124 to be converted to corresponding digital signals which are applied by a parallel bus 191 to port A of the parallel pheripheral interface 166 and therefrom by a data bus 160 to the computer 130. In similar fashion, the series of pulses outputted by the flow meter 26 is applied to the digital flow meter pulse counter 132, which counts the inputted pulses to provide a digital output indicative thereof; the counter output is applied via parallel bus 193 to the parallel pheripheral interface 166 and therefrom via the data bus 160 to the computer 130. The counting of the output pulses from the flow meter 26 is under the control of a computer clock as taken from its output and applied to series connected dividers 172 and 174 to apply a timing signal of a defined period to one input of a NAND gate 176, whereby the output pulses of the flow meter 26 are applied to be counted by the counter 132 for that period, e.g., approximately 7.5 second, corresponding to when the output of the divider 174 goes high. Thus, the counter 132 provides a digital output indicative of the counted pulses during the defined period via a bus 193, the parallel pheripheral interface 166 and the data bus 160 to the computer 130, the number of pulses for a defined period of time being indicative of the flow rate through the tube 12. The flip flop 170 is also connected to the output of the divider 174 to provide a reset signal to the counter 132 and to provide an advance or timing signal to the interrupt input $\overline{\text{INT}}$ of the computer 130. The flip flop 168 provides a necessary interface between the analog to digital conversion as effected by the A/D converter 134 and the program to ensure that outputs are applied in discrete timing periods to the computer 130. The A/D converter 124 provides at the end of its conversion operation an output appearing on its EOC terminal indicating that an analog to digital conversion has been completed; the EOC output is applied to the clock CLK input of the flip flop 168. Upon the addressing of the analog multiplexer 110, an output is also applied via line 190a to set the flip flop 168. Upon the addressing of the analog multiplexer 110, an output is also applied via line 190a to set the flip flop 168. Thus if the A/D converter 124 completes its processing, its EOC signal will clock the flip flop 168 causing its $\overline{\text{Q}}$ output to go high telling port B that a digital input is also available at port A of the parallel peripheral interface 166. A voltage reference source 178 is connected to an available 12 volt terminal, to provide a stable reference voltage to the A/D converter 124. In an illustrative embodiment of this invention, the parallel pheripheral interface 166 is a circuit as manufactured by Intel Corporation under their designation number 8255, the counter 132 is manufactured by the Motorola Corporation under their designation number 14553, the A/D converter 124 is manufactured by the Motorola Corporation under their designation number 14433, the analog multiplexer 110 is manufactured by the Motorola Corporation under their designation number 14051, the dividers 172 and 174 are manufactured by the Motorola Corporation under their designation numbers 14020 and 14040, the flips flops 168 and 170 are manufactured by the Motorals Corporation under their designation number SN74LS74, and the voltage reference source 178 is manufactured by National Semiconductor under their designation number LM399.

Figure 3:
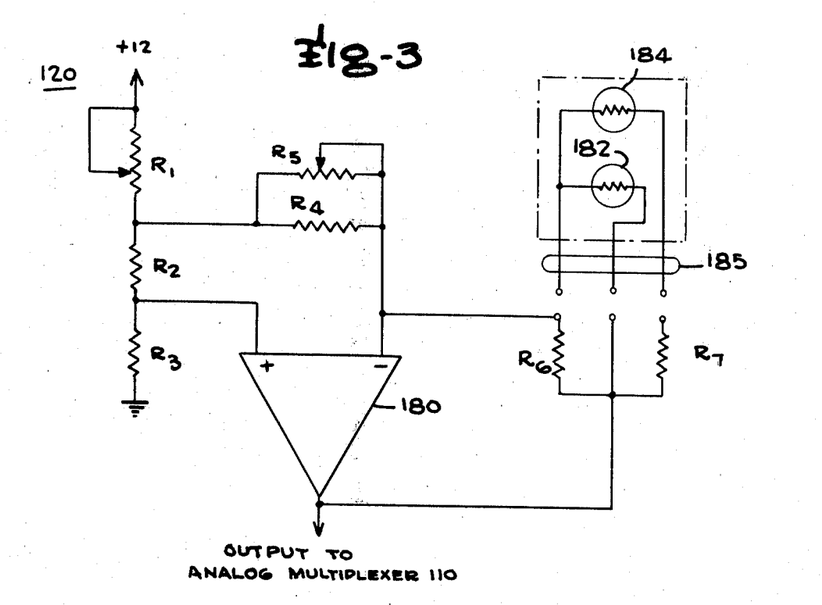
FIG. 3 is a diagram of the thermistor amplifier.

Referring now to FIG. 3, there is shown a circuit for linearizing the output of each of the temperature sensors including the thermometers 28a and 28b, and the thermistors 42 and 44. It is understood that the circuit of FIG. 3 is interconnected between a temperature sensor and its input to the analog multiplexes 110. In particular, each of the aforementioned temperature sensors is comprised of thermistors 182 and 184, that are coupled by a shielded cable 185 to an operational amplifier 180, as manufactured by National Semiconductor Corporation under their designation number LM324. The plus input of the operational amplifier 180 receives a reference voltage as established by a resistance bridge comprised of potentiometer R1, resister R2 and resister R3. The negative input of the operational amplifier 180 is coupled to a potentiometer R5 and resister R4, as well as to the shielded cable 185. In a manner well known in the art, the potentiometer R5 establishes the zero potential, whereas, potentiometer R1 establishes the range of temperature input signals. Resisters R6 and R7 are connected in circuit with the shielded cable 185 and the operational amplifier 180 as shown in FIG. 4, to thereby compensate for the inherent nonlinearity of the thermistors 184 and 182.

Figure 4:
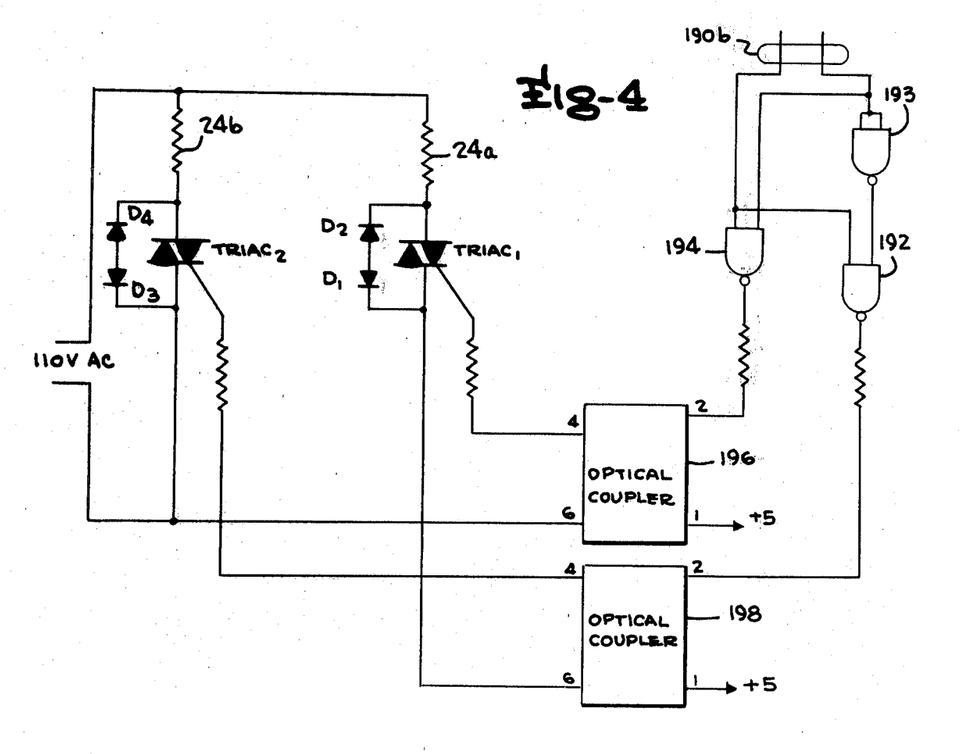
FIG. 4 is a diagram of the circuit for controlling the motorized by-pass valve.

The address and control signals of lines 190c are applied to the motor valve control circuit 24' as shown in FIG. 4 and in particular to the inputs of NAND gates 193 and 194. A logic circuit is formed by the NAND gates 193, 194 and 192 as shown in FIG. 4 to provide outputs to optical couplers 196 and 198, illustratively taking the form of couplers manufactured by Motorola under their designation numbers MOC3010. Firing outputs are developed by the optical couplers 196 and 198 and are applied respectively to the firing terminals of each TRIAC 1 and 2, whereby the TRIAC are rendered conductive to apply an alternating voltage, e.g. 110 volts AC, to the selected motor winding 24a or 24b of the reversible, induction motor driving the bypass valve 24 as shown in FIG. 1. Illustratively, the bypass valve motor may take the form of that induction motor as manufactured by W. W. Graingers as under their number P/N 2Z813. For example, upon the firing of the TRIAC 1, the coil 24a is energized to close the bypass valve 24, thus increasing the fluid flow through tube 12. Conversely, when the TRIAC 2 is fired, its winding 24b is energized, whereby the bypass valve is opened, thus reducing the fluid flow through tube 12. If a binary signal 1,1 is applied by line 190c to the valve control circuit 24', a low going signal will be applied to the optical coupler 196, whereby TRIAC 1 is fired and its winding 24a is energized. On the other hand, if a digital signal 1,0 is applied to the valve control circuit 24', the optical coupler 198 fires TRIAC 2 and energizes the winding 24b.

The computer 130, as shown in FIG. 1, has a programmable storage area in the form of a random access memory (RAM) that is programmed to access the various variables as discussed above, including the fluid flow as obtained from the flow meter 26, and the values of temperature as obtained from the thermometers 28a and 28b, and from the thermistors 42 and 44, and to effect a series of calculations in accordance with the formulas, as given above. To this end, the RAM of the computer 130 is programmed with a program, a listing of which is provided as follows:

```
]LIST

5   HIMEM: 12799
7   RESTORE
10  REM            INSERT MACHINE LANG
               UAGE SUBROUTINES
15  RESTORE
18  REM FLOW METER SUB AT 3200HEX
        :12800DEC
20  REM CK INTERUPT SUB AT 322AHE
        X:12842DEC
22  REM A/D ROUTINE AT 3245HEX:12
        869DEC
24  REM C-PORT OUTPUT AT 32A7HEX:
        12967DEC
26  REM INT DISABLE RESET AT 32A3
        HEX:12963DEC
28  REM  RESET STACK POINTER AT 3
        2B9HEX:12985DEC
30  DATA 160,0,169,32,141,3,63,24
        ,110,3,63,173,145,192,170,45
        ,3,63,77,3,63,240,244,138,41
        ,15,153,0,63,200,46,3,63,46,
        3,63,144,226,96
31  DATA 0,0,0,120,238,32,63,208,
        8,238,33,63,208,3,238,34,63,
        169,239,32,138,50,173,69,0,8
        8,64,0,0,0,169,0,141,31,63,1
        69,254,32,138
32  DATA 50,160,0,169,16,141,17,6
        3,173,144,192,170,45,17,63,2
        40,247,138,41,15,153,18,63,2
        00,24,46,17,63,144,234,173,1
        45,192,41,128,240,15,173,31
33  DATA 63,201,1,240,13,169,1,14
        1,31,63,76,74,50,169,0,141,3
        1,63,96,0,0,141,4,63,169,0,1
        41,5,63,32,167,50,169,255,77
        ,4,63,141,5
34  DATA 63,32,167,50,96,0,0,88,9
        6,0,0,173,4,63,45,6,63,13,5,
        63,141,6,63,141,146,192,96,0
```

```
     ,0,104,168,104,162,252,154,7
     2,152,72,96
35   DATA 0,0
36   FOR N = 12800 TO 12996
37   READ H%: POKE N,H%
38   NEXT N
40   REM INITIALIZE ERROR FLAG AND
       CLOCK REGISTERS
45   FOR N = 16159 TO 16162: POKE
       N,0: NEXT
50   REM INITIALIZE PPI AND IAK
55   POKE 49299,146: POKE 49298,17
       : POKE 16134,17
60   REM SET UP INTERRUPT SUBROUTI
       NE JUMP
65   POKE 1022,42: POKE 1023,50
70   REM RESET INT DISABLE FLAG
71   CALL 12963
72   GOTO 100
73   HOME
75   GOSUB 1010
76   PRINT "HOURS"
77   PRINT HRS
80   GOSUB 1150
81   PRINT "PULSES"
82   PRINT PULSES
83   VSEL = 0
85   GOSUB 1200
86   PRINT "VOLTS"
87   PRINT V
88   Y = Y + PEEK (16159): PRINT "
       ERRORS";Y
90   FOR I = 1 TO 700
92   NEXT I
94   GOTO 73
100  REM            MAIN PROGRAM
105  REM      LOAD CONSTANTS AND
                             TABLES
110  FI = 50:F = 762:TIME = 0
115  DIM A(12),A$(12),B$(12)
120  DATA BULK WATER TEMP IN,DEG-
       C,BULK WATER TEMP OUT,DEG-C,
       INNER BLOCK TEMP,DEG-C,OUTER
       BLOCK TEMP,DEG-C,PRESSURE D
       IFF.,CM-HG,FLOW RATE,M/SEC,U
       -BLOCK,WATTS/M2-DEGC,U-BULK,
       WATTS/M2-DEGC,REYNOLDS NO.,,
       FRICTION FACTOR,E-02
125  FOR N = 1 TO 10: READ A$(N):
       READ B$(N): NEXT
150  REM     LOAD DEFAULT VALUES
155  DF = .1:TFLAG = 0:ITVL = 60
180  REM      DEFINE FUNCTIONS
185  DEF  FN DP(V) = INT (100 *
       V + .5) / 100
```

```
200  REM DISPLAY MENU
205  HOME : VTAB (4): PRINT  TAB(
     10);"--------FFM MENU-------
     -": PRINT
210  PRINT  TAB( 10);"1) MEASURE,
     DISPLAY,RECORD"
220  PRINT  TAB( 10);"2) CALIBRAT
     E PRESSURE DIFF."
225  PRINT  TAB( 10);"3) CALIBRAT
     E THERMISTORS"
230  PRINT  TAB( 10);"4) SET FLOW
     RATE"
235  PRINT  TAB( 10);"5) SET RECO
     RDING FREQ."
240  GOSUB 1055
245  IF SEL < >  - 1 THEN  ON SE
     L GOTO 300,700,800,900,950
250  GOTO 240
300  REM      MEASURE, DISPLAY, REC
     ORD
305  HOME
350  REM      GET TEMPERATURES
355  S$ = "TEMPERATURES": GOSUB 13
     00
360  FOR VSEL = 0 TO 3: GOSUB 101
     0
365  GOSUB 1200
370  TF = 50: IF VSEL > 1 THEN TF =
     25
375  T(VSEL) = TF * V
380  NEXT
395  REM      GET PRESSURE DIFFEREN
     CE
400  S$ = "PRESSURE": GOSUB 1300
405  PRESSURE = 0:VSEL = 4
410  FOR N = 0 TO 9: GOSUB 1010
415  GOSUB 1200
420  PRESSURE = PRESSURE + 2 * V
425  NEXT :PRESSURE = PRESSURE /
     10
430  REM      GET FLOW RATE
433  S$ = "FLOW": GOSUB 1300
435  GOSUB 1150
440  RFLOW = .01025 * PULSES
450  REM      CALCULATE HEAT TRANSF
     ER COEF.
453  IF T(3) - T(1) = 0 THEN UBLO
     CK =  - 1:UWTER =  - 1: GOTO
     460
455  UBLOCK = 1423.4 * (T(3) - T(2
     )) / (T(3) - T(1)):UWTER = 1
     096 * RFLOW * (T(1) - T(0)) /
     (T(3) - T(1))
460  REM      CALCULATE FRICTION FA
     CTOR
```

```
463  IF RFLOW = 0 THEN FF = - 1:
     GOTO 467
465  FF = .2102 * PRESSURE / RFLOW
     ^ 2
467  RE = 10687 * RFLOW / EXP ( -
     .01982 * T(2))
470  REM    FEEDBACK CONTROL OF FL
     OW RATE
500  REM    RECORD DATA
503  S$ = "DATA RECORD": GOSUB 130
     0
505  A(0) = HRS:A(1) = T(0):A(2) =
     T(1):A(3) = T(2):A(4) = T(3)
     :A(5) = PRESSURE:A(6) = RFLO
     W:A(7) = UBLOCK:A(8) = UWTER
     :A(9) = RE:A(10) = FF
506  GOTO 520
510  GOSUB 1010: IF TFLAG = 1 THEN
     POKE 49241,0: STORE A: POKE
     49240,0:TIME = TIME + ITVL
520  REM    VIDEO OUTPUT
525  VTAB (1): PRINT  TAB( 7);"--
     ----FIELD FOULING MONITOR---
     ---": PRINT
530  PRINT  TAB( 10);"RUNTIME IS
     "; FN DP(HRS);" HRS";: CALL
     - 868: PRINT : PRINT
555  FOR N = 1 TO 10: GOSUB 1350:
     NEXT
595  GOTO 350

700  REM    CALIBRATE DIFFERENTIA
     L PRESSURE
705  HOME
710  VSEL = 4
715  GOSUB 1010
720  GOSUB 1200
725  PRESSURE = 2 * V
735  VTAB 10: PRINT "PRESSURE IS:
     ";: CALL  - 868: PRINT  FN
     DP(PRESSURE)
740  GOTO 710
800  REM    CALIBRATE THERMISTORS

805  T$(0) = "TBULK-I":T$(1) = "TB
     ULK-O":T$(2) = "TBLOCK-I":T$
     (3) = "TBLOCK-O"
810  HOME : VTAB 3: PRINT "THERMI
     STOR DESIGNATIONS ARE :"
815  FOR N = 0 TO 3
820  PRINT  TAB( 5);T$(N);" = ";N

825  NEXT
830  VTAB 9: PRINT "ENTER THERMIS
     TOR DESIGNATION FOR NEW SELE
     CTION"
```

```
840 SEL = - 1: GOSUB 1055: IF SE
    L < > - 1 THEN T = SEL
845 VSEL = T
855 GOSUB 1200
860 TEMP = 20.01 + 4.933 * V + 5.
    521 * V ^ 2 - 2.9389 * V ^ 3
    + .73467 * V ^ 4
865 VTAB (12): CALL - 868: PRINT
    T$(T);" = "; FN DP(TEMP)
866 PRINT V
870 GOTO 840
900 REM      SET FLOW RATE
905 HOME : VTAB 10: INPUT "REQUI
    RED FLOW RATE IS ?";SFLOW
910 GOTO 200
950 REM      SET RECORDING FREQ.
955 HOME : VTAB 10: INPUT "ENTER
     REQUIRED RECORDING INTERVAL
     IN MINUTES  ";ITVL
960 IF ITVL < 5 THEN  PRINT "PLE
    ASE ENTER A VALUE >= 5 MIN":
     FOR N = 0 TO 3000: NEXT : GOTO
    955
965 GOTO 200
1000 REM              SUBROUTINES
1010 REM     'ESC',CLOCK CHECK,
              AND TRIAC REFRESH .
1020 CK = 16.4 / 3600
1023 HRS = CK *  PEEK (16160) + 2
     56 * CK *  PEEK (16161) + 65
     536 * CK *  PEEK (16162)
1024 HRS = ( INT (HRS * 1000 + .5
     55)) / 1000
1026 TFLAG = 0: IF 60 * HRS > =
     TIME THEN TFLAG = 1
1040  VTAB 21: PRINT "PRESS 'ESC'
      FOR MENU":SEL = - 1: GOSUB
     1100
1045  IF SEL = 155 THEN  CALL 129
     85: GOTO 205
1050  RETURN
1055  REM     GET A KEYBOARD SELEC
     TION
1060  PRINT : VTAB 20: PRINT "WHA
     T IS YOUR SELECTION?"
1065  GOSUB 1010
1070  IF SEL > 175 AND SEL < 185 THEN
     SEL = SEL - 176: CALL - 868
     : RETURN
1075  IF SEL < > - 1 THEN  VTAB
     20: CALL - 868: PRINT "WRON
     G KEY - TRY AGAIN": FOR N =
     0 TO 2000: NEXT : GOTO 1065
1080  RETURN
1100  REM     LIVE KEYBOARD MONITO
     R
```

```
1110 P =  PEEK (49152): POKE 49168,0
1115  IF P > 128 THEN SEL = P
1120  RETURN
1150  REM    FLOW RATE INTERFACE
1155  CALL 12800
1160 PULSES =  PEEK (16128) + 16 *
      PEEK (16129) + 256 *  PEEK
      (16130)
1165  RETURN
1200  REM    DIGITAL VOLTMETER INT
      ERFACE
1205 CSEL = 2 * VSEL: POKE 16133,
      CSEL
1210  POKE 16132,241
1215  CALL 12967
1240  FOR W = 0 TO 200: NEXT
1245  CALL 12869
1260 VI =  PEEK (16146)
1265  IF VI = 7 OR VI = 3 THEN V =
      9999: GOTO 1290
1275 MSD = 0: IF VI < 8 THEN MSD =
      1
1280 V = (MSD * 1000 +  PEEK (161
      47) * 100 +  PEEK (16148) *
      10 +  PEEK (16149)) / 1000
1285  IF VI = 0 OR VI = 10 OR VI =
      11 THEN V =  - V
1290  RETURN
1295  REM    VIDEO OUTPUT PRINTER

1300  VTAB 23: PRINT "GETTING ";S
      $;: CALL  - 868: PRINT
1305  RETURN
1350  PRINT  TAB( 3);A$(N);" = ";
      FN DP(A(N));" ";B$(N);: CALL
      - 868: PRINT
1355  RETURN
3200 L
3365  GOSUB 1230
```

The machine language subroutines are:

]
]CALL-151

*3200LLLLL

```
3200-   A0 00        LDY   #$00
3202-   A9 20        LDA   #$20
3204-   8D 03 3F     STA   $3F03
3207-   18           CLC
3208-   6E 03 3F     ROR   $3F03
320B-   AD 91 C0     LDA   $C091
320E-   AA           TAX
320F-   2D 03 3F     AND   $3F03
```

```
3212-   4D 03 3F    EOR     $3F03
3215-   F0 F4       BEQ     $320B
3217-   8A          TXA
3218-   29 0F       AND     #$0F
321A-   99 00 3F    STA     $3F00,Y
321D-   C8          INY
321E-   2E 03 3F    ROL     $3F03
3221-   2E 03 3F    ROL     $3F03
3224-   90 E2       BCC     $3208
3226-   60          RTS
3227-   00          BRK
3228-   00          BRK
3229-   00          BRK
322A-   78          SEI
322B-   EE 20 3F    INC     $3F20
322E-   D0 08       BNE     $3238
3230-   EE 21 3F    INC     $3F21
3233-   D0 03       BNE     $3238
3235-   EE 22 3F    INC     $3F22
3238-   A9 EF       LDA     #$EF
323A-   20 8A 32    JSR     $328A
323D-   AD 45 00    LDA     $0045
3240-   58          CLI
3241-   40          RTI
3242-   00          BRK
3243-   00          BRK
3244-   00          BRK
3245-   A9 00       LDA     #$00
3247-   8D 1F 3F    STA     $3F1F
324A-   A9 FE       LDA     #$FE
324C-   20 8A 32    JSR     $328A
324F-   A0 00       LDY     #$00
3251-   A9 10       LDA     #$10
3253-   8D 11 3F    STA     $3F11
3256-   AD 90 C0    LDA     $C090
3259-   AA          TAX
325A-   2D 11 3F    AND     $3F11
325D-   F0 F7       BEQ     $3256
325F-   8A          TXA
3260-   29 0F       AND     #$0F
3262-   99 12 3F    STA     $3F12,Y
3265-   C8          INY
3266-   18          CLC
3267-   2E 11 3F    ROL     $3F11
326A-   90 EA       BCC     $3256
326C-   AD 91 C0    LDA     $C091
326F-   29 80       AND     #$80
3271-   F0 0F       BEQ     $3282
3273-   AD 1F 3F    LDA     $3F1F
3276-   C9 01       CMP     #$01
3278-   F0 0D       BEQ     $3287
327A-   A9 01       LDA     #$01
327C-   8D 1F 3F    STA     $3F1F
327F-   4C 4A 32    JMP     $324A
3282-   A9 00       LDA     #$00
```

```
3284-    8D 1F 3F    STA    $3F1F
3287-    60          RTS
3288-    00          BRK
3289-    00          BRK
328A-    8D 04 3F    STA    $3F04
328D-    A9 00       LDA    #$00
328F-    8D 05 3F    STA    $3F05
3292-    20 A7 32    JSR    $32A7
3295-    A9 FF       LDA    #$FF
3297-    4D 04 3F    EOR    $3F04
329A-    8D 05 3F    STA    $3F05
329D-    20 A7 32    JSR    $32A7
32A0-    60          RTS
32A1-    00          BRK
32A2-    00          BRK
32A3-    58          CLI
32A4-    60          RTS
32A5-    00          BRK
32A6-    00          BRK
32A7-    AD 04 3F    LDA    $3F04
32AA-    2D 06 3F    AND    $3F06
32AD-    0D 05 3F    ORA    $3F05
32B0-    8D 06 3F    STA    $3F06
32B3-    8D 92 C0    STA    $C092
32B6-    60          RTS
32B7-    00          BRK
32B8-    00          BRK
32B9-    68          PLA
32BA-    A8          TAY
32BB-    68          PLA
32BC-    A2 FC       LDX    #$FC
32BE-    9A          TXS
32BF-    48          PHA
32C0-    98          TYA
32C1-    48          PHA
32C2-    60          RTS
32C3-    00          BRK
```

Particular attention is drawn to lines 300 to 595 of the above given program listing wherein the primary data gathering and calculating steps of the program are set out. In particular, on program line 350, an instruction is provided to be executed by the computer 130 to sample the temperature sensors including the thermometers 28a and 28b, and the thermistors 42 and 44, each of the sensors providing outputs identified by a letter T(0) to T(3) in the listing. As explained above, the computer 130 provides a digital signal via the address bus 164, the interface 166 and the bus 190 to direct the analog multiplexer 110 to access serially the forementioned sensors, their temperature values T(0) to T(3) being stored in known RAM locations. Next, as indicated beginning at program line 395, the output of the differential pressure transducer 160 is accessed and a digital indication of the pressure difference is stored in RAM. Similarly at line 430, the output of the counter 132 is accessed and a computation at line 440 is effected, whereby the flow rate in meters per second is calculated and stored in a known RAM location. Next, beginning at computer line 450, the heat transfer coefficient, i.e., the reciprocal of the total heat transfer resistance $1/U_{tot}$ as defined above, is calculated at program line 455, where T(0) indicates the stored value of the bulk water temperature as measured by the thermometer 28a, T(1) indicates the water temperature measured by the thermometer 28b, T(2) and T(3) indicate the values of temperature as measured respectively by the thermistors 42 and 44, and "RFLOW" is the measured value of flow rate as obtained from the counter 132. Thus, program line 455 indicates that the heat transfer coefficient is calculated from the aforementioned values and thereafter restored in a known RAM location. Next, at computer line 460, the friction factor "f", as set out above, is calculated. Program line 465 indicates that the friction factor "f" is computed as a function of the pressure drop as measured by the transducer 60, and the square of the fluid flow as derived from the flow meter 26. At program line 467, the Reynold's number $N_{Re}$, as given above, is calculated by multiplying the value of fluid flow times an exponential taken to the value T(1) of the bulk water temperature as measured by the thermometer 28a. At line 505, a data array is formed within the RAM to provide various value of temperature and flow rate.

The above provided listing does not set out a set of steps for calculating the values of the convective heat transfer resistance $1/U_{conv}$ as provided by formula 4 is calculated at computer line 465, and the Reynold's number $N_{Re}$ is calculated at line 467. Thereafter the calculation would be executed to take the difference between the convective heat transfer resistance $1/U_{conv}$ and the reciprocal of the heat transfer coefficient, i.e., the total heat transfer resistance $1/U_{tot}$, calculated at computer line 450. As indicated above, the value of $1/U_{cond}$ of the conductive heat transfer resistance is indicative of the degree of fouling within the tube 12 and would be either automatically or at the command of an operator entered by the keyboard 144, would be displayed upon the video output 160.

What is claimed is:

1. Apparatus for measuring heat transfer characteristics of a tube comprising:
    (a) a tube,
    (b) a source of pressure for forcing liquid such as water through said tube,
    (c) means for heating at least a portion of said tube,
    (d) means for determining the heat flux supplied to said tube by said heating means,
    (e) means for determining the temperature of the liquid in said tube, and
    (f) means for determining the friction factor of said tube.

2. The apparatus of claim 1, and further comprising a block of heat conducting material in surrounding engaging relationship with said portion of said tube, said heating means comprising means for supplying heat energy to said block for causing heat to flow therethrough to said tube.

3. The apparatus of claim 2, said means for determining the heat flux to said tube comprising at least two heat measuring means in said block at different distances from said heat supplying means.

4. The apparatus of claim 1 or 3, and further comprising means for generating an output signed proportional to heat flux, means for generating an output signal proportional to water temperature, and means for calculating total heat transfer resistance from said last two mentioned output signals.

5. The apparatus of claim 1, said means for determining the friction factor of said tube comprising means for determining the pressure drop of the liquid in the said portion of the tube, and means for measuring the rate of flow of liquid through said tube.

6. The apparatus of claim 5, and further including means for generating an output signal proportional to the said pressure drop, means for producing an putput signal proportional to the rate of flow of the liquid, and means for receiving said pressure drop and flow rate output signals and for calculating the friction factor of said tube.

7. The apparatus of claim 1 or 2, and further comprising means for generating an output signal proportional to the water temperature, means for generating an output signal proportional to the flow rate, and means for receiving said last two mentioned signals and for calculating the Reynolds number of the liquid flowing in said tube.

8. The apparatus of claim 1, and further comprising means for measuring the flow rate in said tube and for generating a signal proportional thereto, means for generating output signals proportional to water temperature and friction factor, and means for receiving said output signals and for calculating the convective heat transfer resistance of said tube.

9. The apparatus of claim 8, and further comprising means for generating an output signal proportional to heat flux, means for calculating total heat transfer resistance from heat flux and from water temperature signals, means for generating an output signal proportional to convective heat transfer resistance, and means for calculating conductive heat transfer resistance from convective and total heat transfer resistance signals.

10. The apparatus of claim 1, said source of pressure comprising a pump, and conduit means connecting the outlet of said pump with the inlet of said tube, and conduit means connecting the outlet of said tube with the inlet of said pump.

11. The apparatus of claim 10, and further including by-pass conduit means around such pump, and a valve in said by-pass conduit means.

12. For the apparatus of claim 1, and further including insulation means on substantially the entire length of said tube, and additional heating means extending between said tube and said insulation along said tube other than at the location of said first mentioned heating means.

13. The apparatus of claim 1 or claim 5, and further comprising a heat exchanger having tubes therein, means connecting said tube in parallel with the tubes of said heat exchanger tubes.

14. Apparatus for providing a manifestation indicative of the deposition from a liquid of a fouling material upon an inner surface of a tube by the liquid flowing therethrough, said apparatus comprising:
    (a) a tube:
    (b) means for directing the fluid through said tube;
    (c) means disposed about a portion of said tube means for applying thermal energy to an outer surface of said portion of said tube means;
    (d) means for measuring the temperature of the fluid as it passes through said portion of said tube means to provide a first manifestation thereof;
    (e) means for determining the pressure drop of the fluid as it passes through said portion of said tube means to provide a second manifestation thereof;
    (f) means for measuring the rate of flow of the liquid as it passes through said tube means to provide a third manifestation thereof;
    (g) means associated with said thermal means for determining the heat flux at said outer surface of said tube means to provide fourth manifestation thereof; and
    (h) calculating means for providing a manifestation indicative of the conductive heat transfer resistance of the fouling deposit on said interior surface of said tube means, said calculating means comprising means responsive to said second and third manifestations for determining the friction factor "f" as presented to the liquid flowing through said tube means by said fouling deposit on said interior surface of said tube means, means responsive to said first manifestation and said third manifestation for providing an indication of the Reynolds number of the fluid passing through said tube means, mean responsive to said first, third and fourth manifestations for providing a manifestation indicative of the total heat transfer resistance of the fouling deposit, and means responsive to said friction factor indication and the Reynolds number to provide a manifestation of the convective heat transfer resistance of the heat passing through the fouling deposit, and means for providing a manifestation indicative of the convective heat transfer resistance of the fouling deposit as the difference between said total heat transfer resistance manifestation and said convective heat transfer resistance manifestation.

* * * * *